United States Patent [19]
Lindenberg et al.

[11] Patent Number: 5,507,729
[45] Date of Patent: Apr. 16, 1996

[54] ONE-PIECE GUIDE PART AND PROCESS FOR THE PRODUCTION THEREOF

[75] Inventors: Josef Lindenberg; Wolfram Schnepp-Pesch, both of Karlsruhe, Germany

[73] Assignee: Angiomed AG, Karlsruhe, Germany

[21] Appl. No.: 188,013

[22] Filed: Jan. 28, 1994

[30] Foreign Application Priority Data

Jan. 28, 1993 [DE] Germany ........................ 43 02 326.6
May 15, 1993 [DE] Germany ........................ 43 16 330.0

[51] Int. Cl.$^6$ ........................................ A61M 5/178
[52] U.S. Cl. ........................................ 604/170; 128/772
[58] Field of Search ........................ 128/772, 657; 604/95, 170

[56] References Cited

U.S. PATENT DOCUMENTS

| | | | |
|---|---|---|---|
| 3,452,742 | 7/1969 | Muller | 128/772 |
| 4,664,113 | 5/1987 | Frisbie et al. | 128/772 |
| 4,796,642 | 1/1989 | Harris | 128/772 |
| 4,827,941 | 5/1989 | Taylor et al. | 128/772 |
| 4,925,445 | 5/1990 | Sakamoto et al. | 128/772 |
| 4,991,602 | 2/1991 | Amplatz et al. | 128/772 |
| 5,299,580 | 4/1994 | Atkinson et al. | 128/772 |
| 5,313,967 | 5/1994 | Lieber et al. | 128/772 |

FOREIGN PATENT DOCUMENTS

| | | |
|---|---|---|
| 401158 | 12/1990 | European Pat. Off. . |
| 515201 | 11/1992 | European Pat. Off. . |
| 8900077 U | 3/1993 | Germany . |
| 15152 | 10/1991 | WIPO . |

*Primary Examiner*—Stephen C. Pellegrino
*Assistant Examiner*—Nancy Mulcare
*Attorney, Agent, or Firm*—Antonelli, Terry, Stout & Kraus

[57] ABSTRACT

Guide wires for the medical field and which are e.g. used for the introduction of catheters, locks, etc. into the human body and in particular into vessels and organs are disclosed. To avoid the risk of a detachment of parts, the guide wire is provided as a one-piece, highly flexible material guide wire, which has a proximal end portion with a first thickness and following onto the same at least one cross-sectional reduction for increasing the bending flexibility at least in an area connected to the proximal end portion and which in the distal end portion remote from the proximal end portion has portions with a cross-section of the same order of magnitude as that of the proximal end portion. According to a preferred process for producing such a guide wire, a rod-shaped part with a smooth outer wall is drawn continuously and at least once over part of its length from an etching bath attacking its material into a non-etching environment.

11 Claims, 1 Drawing Sheet

ONE-PIECE GUIDE PART AND PROCESS FOR THE PRODUCTION THEREOF

FIELD OF THE INVENTION

The invention relates to a catheterization guide wire made from flexible material as well as to a process for the production thereof.

BACKGROUND OF THE INVENTION

Guidewires are generally used as guide wires in the medical field for the introduction of parts into the human body and, in particular, into vessels or organs thereof. By means of such guide wires it is possible to introduce and, optionally fit into the human body, catheters, locks, implantable catheters (stents), cannulas, etc.

Known guide wires comprise one or more helically wound strands and, in the case of a wound strand, the helixes generally have a very limited pitch, whereas several wires are often twisted with a high pitch. The front insertion end of such a guide wire is blunted and is provided there with a bead, cap, etc. The latter is held by a fine locking wire extending within the helix and is welded thereto. Such a guide wire is in several parts and has the aforementioned, as well as further weld points. Such welds are predetermined breaking points, because they cam break in the case of a limited loading or stressing due to fatigue phenomena thereof. A further weak point is constituted by the thin locking filament, because the latter only has a very limited diameter. There is a further considerable risk that at the helixes in the area between two turns, hooking together can occur as a result of the acute angle of the opening area between the two turns of other parts used during the introduction process, such as cannulas, particularly when they are provided with obliquely ground ends and as a result there can be a breaking of the guide wire or of the helical wire or wires. A danger exists that parts of the guide wire can become detached and remain in the body, such cases being known.

SUMMARY OF THE INVENTION

The aim of the invention is to provide a guide wire which avoids the aforementioned disadvantages and reduces by several powers of 10 the risk of these occurring. The further aim of the invention is to provide a process for the production of such a guide wire.

In accordance with the present invention, the guide wire is constituted as a one-piece, elastic material guide wire, which has a front insertion end having a first thickness, at least one cross-sectional reduction following onto the insertion end and at least one portion having a cross-section of the sane order of magnitude as the insertion end in the rear area remote from the latter and in the vicinity of the cross-sectional reduction the wire diameter is reduced to less than half the maximum diameter. In processes for the production of such a guide wire, a rod-shaped, one-piece part with a smooth outer wall and made from flexible metal is ground in partial regions for producing cross-sectional reductions and a one-piece, rod-shaped part with a smooth outer wall made from flexible metal at least once and at least over part of its length is continuously drawn from an etching bath attacking its material into a non-etching environment.

Thus, the guide wire according to the invention is made completely in one piece. This obviates the "predetermined breaking point", such as exist in known guide wires, particularly as a result of welds, and consequently the risk of a breakage or tearing away of parts of the guide wires at such points is prevented. In addition, unlike in the case of helically wound guide wires, the one-piece guide wire can be constructed with a smooth surface without undercuts or outer contour regions with acute angles, such as in particular occur with helical guide wires between two adjacent turns. To the extent that the guide wire according to the invention has thickness increases or reductions, they can be in a continuous form. In order to give the guide wire the desired, very high flexibility, more particularly in its front, insertion region, i.e. to give it the high, but reversible and therefore elastic softness and bendability, in said region there are tapered portions, i.e. whose transverse dimensions are reduced compared with the maximum transverse dimensions of the remaining guide wire. As a result of the elastic metallic material, which can be high-grade steel, but is preferably high tensile titanium-nickel alloy (nitinol), the cross-sectional dimensions in the minimum diameter areas can be very small, without inadmissibly reducing the tensile strength. However, it is also possible to use other metal alloy, such as bimetal, etc. According to preferred developments, the minimum diameter is less than a third of the maximum diameter and the minimum diameter is in particular less than a quarter of the maximum diameter. As a result of the smooth wall and the hard metallic material it is ensured that the tip of a sharp cannula does not hook up, or penetrate and lock in the material and/or become damaged.

The transverse dimensions can be such that the transition area extending from the insertion end to the rear region continuously widens and is, in particular, conical. With regards to the length of the transition area, according to a preferred development that the transition area extending from the point of minimum cross-section behind the insertion end and away therefrom is at least ten times as long as the portion from the minimum cross-section point immediately behind the insertion end and up to the end face thereof. Alternatively for increasing the bendability of the guide wire in desired areas the transition area has periodically widening and narrowing portions. The length of the period of widening and narrowing portions can be appropriately selected and has a length between 3 and 9 mm.

According to a preferred development of the invention in a front area extending from its insertion end, the guide wire has etched portions. An essential and unique inventive concept is constituted by the fact that a one-piece guide wire has over its length worn-away and in particular etched-away areas, in which it has a reduced transverse dimension compared with its normal, original transverse dimension and the reduction is brought about by etching.

In preferred manner the guide wire can be constructed in such a way that at least in its front region it assumes a different configuration as a function of the temperature above or below a predetermined temperature range. Therefore such a guide wire has memory characteristics. It can e.g. be made from memory metal, i.e. a metal, such as nickel-titanium alloys, which in the case of temperature changes have a restoring effect to another configuration or contour. Thus, in its low temperature state, i.e. below the transition temperature, such a guide wire can be straight, whereas upon increasing the ambient temperature or its own temperature above the transition temperature an arcuate bending effect can be obtained and vice versa, depending on which contour is required under which conditions.

The front insertion end of the guide wire can be constructed in different ways. Fundamentally and advantageously, in its forwardly directed, free area the insertion end is at least part spherical. According to a further development the insertion end is spherical and has a drop shape or the end is cylindrical, at least over a portion thereof. According to other developments, at least a portion of the insertion end has a polygonal cross-section and, in particular, the guide wire is solid.

The inventive process for the production of such a one-piece guide wire by etching can be further developed in that, prior to the etching stage, at least portions of the rod-shaped part are provided with a coating resistant to the etching bath. According to a further development the rod-shaped part is drawn at a constant speed from the etching bath and is passed through a seal sealing the etching bath against a non-etching environment, either a solid, rod-shaped part being drawn from the etching bath, or a tubular part is drawn out of the etching bath.

According to a further preferred development, the etching bath temperature is kept constant.

The invention leads to a highly flexible guide wire, in which the hardness, particularly the tensionability of the material, can be appropriately adjusted in the same way as the bendability of the front insertion region of the guide wire by an appropriate choice of the wire thickness increases and decreases. As a result of its one-piece construction from a rod-shaped or tubular member, the guide wire has a much higher torsionability, than is the case with known, wound guide wires. A rotary movement at the rear end of the guide wire is in practice directly and completely also performed by the insertion end.

BRIEF DESCRIPTION OF THE DRAWINGS

Further advantages and features of the invention can be gathered from the claims and the following description of two embodiments of the guide wire according to the invention and with reference to the attached drawings, wherein:

DETAILED DESCRIPTION OF THE DISCLOSED EMBODIMENTS

Figure 1:
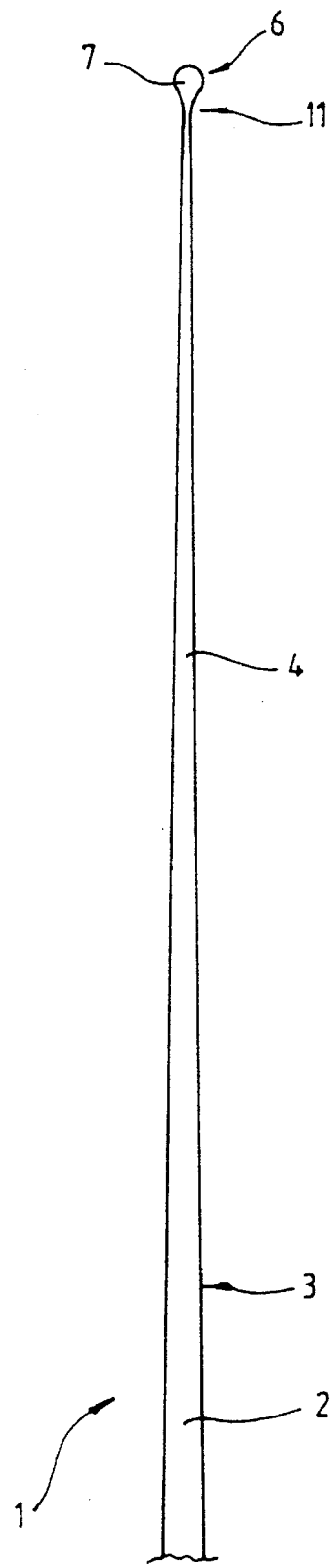
FIG. 1 is a side elevational view of a first embodiment of a guide wire according to the invention.

The guide wire according to the invention, wire 1 as shown, FIG. 1, has a rear or distal main area 2 of a constant cross-section, which extends from its free end, not shown up, to an area 3 and over its entire length, which can be several decimeters to more than 1 m, has a constant cross-section and is circular in the illustrated embodiment. From the area 3 the transition area 4 of the guide wire tapers to close to its front insertion end 6. The tapered area is conical with a very limited, acute angle. At the front insertion end 6, the one-piece guide wire is provided with a widened portion 7, which in the represented embodiment is drop shaped and at the free end is part spherical and at its rear side, like the end of a drop, passes continuously into the conical area 4.

In a preferred embodiment, the maximum guide wire diameter is just below or at 1 mm, while the minimum diameter is 0.2 mm. The length of the transition area is 70 mm, but can e.g. also extend to 250 mm.

As a result of the conical construction, in said transition area the guide wire has a higher bending flexibility than in its constant cross-section area 2, so that the conical transition area 4 can follow all the bends and branches in vessels and organs. Injury is prevented by the rounding of the front widened portion. A locking of a cannula inserted with such a guide wire is virtually impossible.

Figure 2:
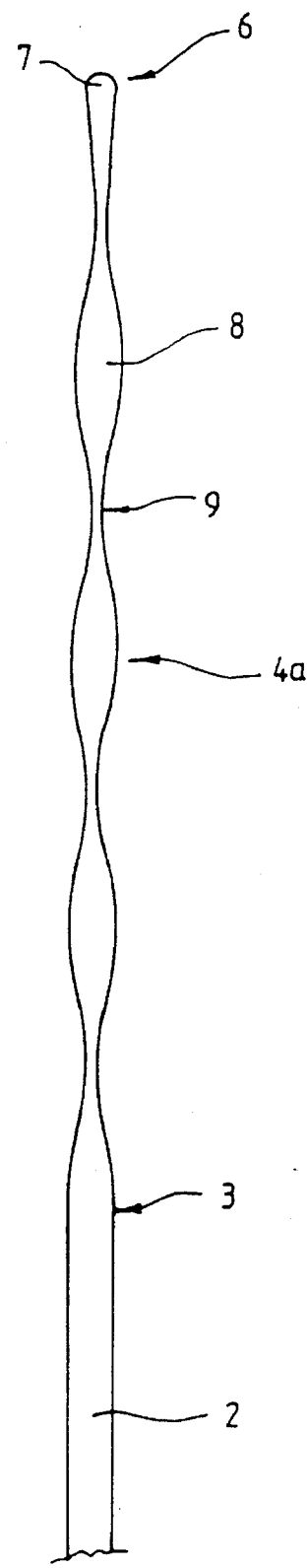
FIG. 2 is a side elevational view of a second embodiment of a guide wire according to the invention.

In the case of the construction of FIG. 2 the rear main area 2 and the insertion end 6 are constructed with the widened portion 7 similar to that of FIG. 1. An increased flexibility in the front area 4a between the main portion 2 and the insertion end 6 is obtained by periodically alternating widened portions 8 and narrow portions 9. The length of a period is 5 mm in a preferred embodiment, but can also be longer.

Although the guide wires have been described as having a circular cross-section, the latter can also be oval or elliptical. The widened portion at the insertion end can be part spherical, dome-shaped, cylindrical with rounded edges and cross-sectionally polygonal, the edges being at least deburred, or can be constructed in some other way.

As a result of the one-piece construction of the guide wire according to the invention, the latter has an extremely high tensile strength, which ensures that portions cannot become detached, this more particularly applying to the widened portion 7. Thus, it was e.g. found during a test, that in the case of the widened portion 7 being drawn into a steel cannula by exerting tension, with an opening of the cannula slightly below the cross-sectional dimensions of the widened portion 7 and with a minimum diameter of the guide wire at its smallest point of 0.25 mm, the widened portion 7 did not tear away and instead widened the cannula opening and consequently the guide wire could be drawn through the latter.

While it is possible to use various different highly flexible materials with a high tensile strength, in preferred manner use is made of nickel-titanium alloys, particularly those known under the name nitinol, because in addition to the high tensile strength, they also have a high elastic bendability and even under much higher forces than occur under normal conditions, cannot be irreversibly, plastically kinked. However, it is also possible to use plastic materials, particularly of a fibre-reinforced form, such as materials reinforced by graphite fibres.

It is also important that the outer contour of the completely one-piece guide wire according to the invention is smooth and that in the vicinity of the transition area there are no acute angles in the outer contour, such as occur with helically wound guide wires, where between two juxtaposed turns the radial aperture between then has an angle towards 0, so that it is possible for the hooking together of objects, such as e.g. the tips of obliquely ground cannulas, which can lead to tearing away.

Whereas the guide wires according to the invention can also be produced by grinding and polishing in the represented manner, in preferred manner this takes place in the case of metallic guide wires, such as nickel-titanium alloy wires, by etching in an etching bath, such as of silicic acid. Over a length range corresponding to the cross-sectional extension from the narrowest point to the widest point, the guide wires are continuously drawn from an etching bath, which leads to the continuous taper. Other areas can be covered and protected by coatings resistant to the etching bath, such as a photolacquer and it is optionally possible to draw through seals. Even if the thickness reductions are obtained by etching, a final treatment by polishing can take place.

Thus, e.g. the guide wire of FIG. 1 is produced in such a way that the area 4 is initially covered by a resistant coating and the rear drop area 11 is produced, in that the front, free end of the guide wire to be produced and having the widened portion 7 is slowly and continuously moved out of an etching bath and the not yet tapered transition area 4 is passed through a seal in the bottom of the etching bath.

Subsequently the insertion end 6 with the widened portion 7 is provided with the protective coating up to the narrowest point, whereas the coating is removed from the tapered area 4. Over the desired length of the area 4, the guide wire is introduced into the etching bath and is then slowly and continuously drawn out of the same up to the rear end 2. As a result, areas of the tapered portion 4 close to the free insertion end 6 remain longer in the etching bath than areas close to the main portion 2, so that the first-mentioned areas are more strongly exposed to the etching bath and therefore receive a greater cross-sectional reduction than the last-mentioned areas. This zonal approach can consequently be used for producing the narrowed and widened portions 8, 9 of the guide wire of FIG. 2.

We claim:

1. A guide wire for catheterization, said guide wire being solid and made in one piece from an elastic metal and including a distal end portion of a constant cross-section and a proximal end portion having a rounded end face which has a maximum diameter greater than a minimum diameter of a transition area conically tapering at least from said distal end portion to said proximal end portion, wherein said transition area continuously widens over its entire length from a minimum cross-section point directly behind said proximal end portion to said distal end portion, and wherein said proximal end portion has at its axial end joining said transition area a shape like the end of a drop which passes continuously into said transition area.

2. The guide wire according to claim 1, wherein said minimum diameter is less than a quarter of said maximum diameter.

3. The guide wire according to claim 1, wherein said transition area extending from the minimum cross-section point behind said proximal end and away from the latter is at least 10 times as long as said proximal end portion which extends from the minimum cross-section point forward to said rounded end face thereof.

4. The guide part according to claim 1, wherein said transition area has a length which is at least 20 times as long as said proximal end portion.

5. The guide wire according to claim 1, wherein said transition area is formed by removing solid material from said guide wire.

6. The guide wire according to claim 4, wherein said removing is accomplished by grinding.

7. The guide wire according to claim 4, wherein said removing is accomplishing by etching.

8. The guide wire according to claim 1, wherein said wire is made from nickel-titanium alloy.

9. The guide wire according to claim 1, wherein at least in the area of said transition area and said proximal end portion said guide wire has a memory property such that as a function of the temperature above or below a given temperature range, said guide wire assumes a different configuration.

10. The guide wire according to claim 1 wherein said rounded end face of said proximal end portion is hemispherical.

11. The guide wire according to claim 1, wherein said proximal end portion as a whole is drop shaped.

* * * * *